United States Patent [19]

Casey

[11] 4,064,564  
[45] Dec. 27, 1977

[54] CHITIN DERIVED SURGICAL GLOVE POWDER

[75] Inventor: Donald James Casey, Ridgefield, Conn.

[73] Assignee: American Cyanamid Company, Stamford, Conn.

[21] Appl. No.: 738,200

[22] Filed: Nov. 3, 1976

[51] Int. Cl.$^2$ .................. A61B 19/04; A41D 19/00
[52] U.S. Cl. ........................... 2/168; 128/260; 128/349 R
[58] Field of Search .................. 2/168; 128/1 R, 221, 128/260, 348, 349 R, DIG. 16; 206/63.3, 210, 363–366, 438–439; 252/12; 424/180; 536/20

[56] References Cited

U.S. PATENT DOCUMENTS

| | | | |
|---|---|---|---|
| 3,728,739 | 4/1973 | Semp | 128/1 |
| 3,810,458 | 5/1974 | Semp | 128/1 R |
| 3,846,382 | 11/1974 | Ramsey et al. | 128/1 R |
| 3,911,116 | 10/1975 | Balassa | 424/180 |

Primary Examiner—Dalton L. Truluck  
Assistant Examiner—Jerome D. Stremcha  
Attorney, Agent, or Firm—Charles F. Costello, Jr.

[57] ABSTRACT

Natural or synthetic rubber surgical elements such as tubing, catheters, drains and gloves are "lubricated" so as to prevent sticking during storage, and permit easier emplacement, such as putting on the gloves by a surgeon or nurse, by applying to the surface of the rubber element
  a finely divided biodegradable powder consisting essentially of
  an enzymatically degradable form of poly(N-acetyl-D-glucosamine) selected from the group consisting of
  poly[N-acetyl-6-O-(carboxymethyl)-D-glucosamine],
  poly[N-acetyl-6-O-(2'-hydroxyethyl)-D-glucosamine],
  poly[N-acetyl-6-O-(ethyl)-D-glucosamine], and
  poly(N-acetyl-D-glucosamine) itself This powder is readily absorbed by living tissue without deleterious tissue reaction, thus minimizing tissue reaction from the transfer of the powder from the element such as a glove to internal sites in a subject. The gloves may be packaged in a strippable laminate package. The polymers are derived from chitin.

6 Claims, 4 Drawing Figures

12 POWDERED ENZYMATICALLY DEGRADABLE FORM OF POLY-(N-ACETYL-D-GLUCOSAMINE) TO LUBRICATE SURFACE

18 CATHETER

CHITIN DERIVED SURGICAL GLOVE POWDER

BACKGROUND OF THE INVENTION

This invention relates to a natural or synthetic rubber surgical glove which is lubricated with a finely divided biodegradable powder consisting essentially of an enzymatically degradable form of poly(N-acetyl-D-glucosamine) selected from the group consisting of poly[N-acetyl-6-O-(carboxymethyl)-D-glucosamine], poly[N-acetyl-6-O-(2'-hydroxyethyl)-D-glucosamine], poly[N-acetyl-6-O-(ethyl)-D-glucosamine], and poly(N-acetyl-D-glucosamine) itself which form of poly(N-acetyl-D-glucosamine) is slowly enzymatically degraded by contact with body tissues. Other rubber elements which contact raw tissue may be similarly lubricated. Various dusting powders have been used on surgical gloves for years with a prime use being to facilitate insertion of the hands of operating room personnel into natural or synthetic rubber or latex gloves worn during surgery.

It is desirable that the powder on the gloves meet the following requirements:
1. It should be non-toxic to living tissue.
2. It should be biodegradable, i.e., absorbed by living tissue. This is most important since, during surgical procedures, powder almost inevitably falls or is rubbed from the surgeon's gloved hand into an exposed body cavity, and may be carried from other areas of the operating room into the exposed body cavity by air currents.
3. The powder should have no adverse effect within the body such as the creation of lesions (i.e., adhesions, granulomas, or such).
4. The glove powder must be capable of sterilization by convenient hospital techniques, preferably both autoclaving and gaseous ethylene oxide sterilization.
5. The powder must possess sufficient lubricity to permit ready insertion of the hand into the glove and must be of sufficiently fine particle size and have characteristics permitting such lubricity.
6. It must be reasonably priced and readily available.
7. It must be non-irritating to skin of both the surgeon or nurse and the patient.
8. Preferably the powder resists hydrolytic degredation.

Talc was among the earliest surgical glove powders used by the medical profession. However, after the report by Antopol (Lycopodium Granuloma, Arch. Path. 16, pg. 326 (1933)) that talc caused granulomas in the body, the use of talc as a glove powder was rapidly abandoned. Talc was replaced by starch glove powders since starch was known to be biodegradable and was not believed to cause granulomas or other aggravating conditions within the body. Currently, a widely used commercial surgical glove powder is specially treated homogeneous amylose which contains about 2 percent magnesium oxide to prevent clumping of the powder.

However, starch glove powders have a number of disadvantages. They offer high resistance to flow and they tend to gelatinize or agglutinate in the presence of hot water thereby creating problems when they are sterilized in a steam autoclave. Ordinarily, the starch must be treated in some way to minimize these properties. For example, as shown in U.S. Pat. No. 2,626,257, the starch may be treated with an agent, such as epichlorohydrin, which partially etherifies the starch in order to make the powder free flowing after steam sterilization.

Starch is also an excellent nutrient medium for virtually all vegetative bacteria such as various pathogenic microorganisms and is objectionable for that reason.

According to Lee and Lehman(Surgery, Gynecology, and Obstetrics 84, pages 689-695 (1947), starch, unlike talc, was completely absorbed within the peritoneal cavity without causing adhesions. This conclusion was challenged by Sneierson and Woo(Annals of Surgery 132, pgs. 1045-1050 (1955) who reported two cases of large granulomas occurring in surgical wounds as a result of starch powder contamination. McAdams(Surgery 39, pgs. 329-336 (1936) reported three cases of intraperitioneal granulomas caused by starch glove powder. The Saxens (Acta Pathology Microbiology Scand. 64, pgs. 55-70 (1965) postulated that the magnesium oxide which acts as an anticlumping material was causing the lesions. Myllarniemi and Frilander (Journal of the International College of Surgeons 44, No. 6681, pgs. 677-681 (1965) concluded that the harmful effects of starch glove powders containing magnesium oxide might be due to a combined effect of two irritating constituents. Other publications which indicate the serious concern of the medical profession over granulomas traced to starch glove powders are those of Lehman and Wilder (Journal of Abdominal Surgery 4, No. 3, pgs. 77-80 (1962), Webb and Regan (Archives of Surgery 84, No. 3, pgs. 282-285 (1962), and Walczak and Collura (American Journal of Surgery 103, No. 5, pgs. 611-612 (1962).

Despite the aforementioned disadvantages associated with starch glove powders, they are still used by the medical profession.

U.S. Pat. No. 3,728,739—B. A. Semp.—April 24, 1973 STERILE SURGICAL GLOVES shows rubber surgical elements such as tubing, catheters, drains and gloves which are lubricated with finely divided polyglycolic acid.

U.S. Pat. No. 3,810,458—Semp.—May 14, 1974 MINIMIZING TISSUE REACTION TO GLOVE POWDER claims a method of minimizing tissue reaction in a surgical procedure by using a rubber surgical element having a lubricity imparting quantity of a finely divided biodegradable polymer containing hydrolytically degradable glycolic acid ester linkages.

U.S. Pat. No. 3,892,314—Semp.—July 1, 1975 STERILE RUBBER GLOVE OR CATHETER PACKAGE describes sterile surgical elements in a strippable laminate container using a finely divided polyglycolic acid or related polymer as a lubricant for the surface of the rubber elements.

U.S. Pat. No. 3,846,382—Ramsey and DeLapp—Nov. 5, 1974 STERILE MEDICAL DUSTING POWDER discloses a method of dissolving polyglycolic acid in hot dimethyl sulfoxide, chilling, filtering, washing with isopropanol and with recovering finely divided polyglycolic acid.

U.S. Pat. No. 3,632,754—Jan. 4, 1972—Balasse—USE OF CHITIN FOR PROMOTING WOUND HEALING teaches the application of a powder or solution of chitin or a chitin derivative to accelerate the rate of wound healing in a mammal.

Application Ser. No. 558,526—Capozza—Mar. 14, 1975, now U.S. Pat. No. 3,988,411 SPINNING AND SHAPING POLY(N-ACETYL-D-GLUCOASAMINE) shows the use of exotic solvents such as hexafluoroisopropyl alcohol and hexafluoroacetone sesquihydrate in the spinning, shaping and extruding of poly(N-acetyl-D-glucosamine). Various surgical uses of the poly(N-acetyl-D-glucosamine) are taught.

SUMMARY OF THE INVENTION

This invention includes a natural or synthetic rubber surgical glove having a lubricating coating of a finely divided biodegradable powder consisting essentially of an enzymatically degradable form of poly(N-acetyl-D-glucosamine) selected from the group consisting of
poly[N-acetyl-6-O-(carboxymethyl)-D-glucosamine],
poly[N-acetyl-6-O-(2'-hydroxyethyl)-D-glucosamine];
poly[N-acetyl-6-O-(ethyl)-D-glucosamine], and
poly(N-acetyl-D-glucosamine) itself The powdered glove may be sterilized by autoclaving with no adverse effect upon the desirable properties of the powder, such as, for example, the ability of the powder to flow freely without clumping. The powder can also be sterilized by other known methods such as, for example, gaseous ethylene oxide sterilization, or radiation. The powder is non-toxic to living tissue and non-irritating to the skin.

The novel powder of this invention provides the medical profession with a lubricant powder which is absorbable by living tissue and which, furthermore, is non-toxic and gives no indication of causing lesions or other aggravating conditions to any substantial degree within the body. The powder is readily sterilized by autoclaving or ethylene oxide vapor and requires no elaborate pre-treatment of the powder to prevent it from clumping during such sterilization treatments, and both before and after sterilization the powder and the lubricated element resist hydrolytic degredation.

Natural rubber or synthetic rubber surgical elements have many uses. Probably the most common is that of a rubber glove used by a surgeon or nurse during a surgical procedure or examination of a patient. Other sterile surgical elements may be used such as catheters, or rubber drainage tubes which are placed in the site of a wound to permit drainage during the healing process. Such drains are often removed as soon as the healing process proceeds to the point that a discharge is no longer occurring. Whether the surgical element such as a drainage tube is to remain in the patient for a matter of several days or whether it is a surgical glove which is to be in contact with the raw tissues of a wound for only a period of a few minutes, any powder on the surface of the rubber may be transferred into the subject. Foreign elements in tissue usually cause adverse reactions. The degree of the adverse reaction can vary over a wide limits but even though the reaction may be minimal, it is desired that it be reduced as far as possible.

To prevent rubber elements from sticking to each other, for example the turns of a rubber tube, or the folds of a surgical glove, it is desirable that the surface be coated with a finely divided powder which imparts lubricity. Lubricity is particularly necessary with a surgeons glove in order that the glove may be easily donned.

Obviously, it is highly desirable that any such lubricating powder be completely non-irritating to the living tissues of the subject. Although the desirability of an inert powder which is completely absorbable has been recognized, a powder which would meet the requirements of lubricity and still be completely absorbable with a minimal tissue reaction under any and all conditions and which is storage stable in the presence of water vapor has been an illusory goal.

It has now been found that the present a finely divided biodegradable powder consisting essentially of
an enzymatically degradable form of poly(N-acetyl-D-glucosamine) selected from the group consisting of
poly[N-acetyl-6-O-(carboxymethyl)-D-glucosamine],
poly[N-acetyl-6-O-(2'-hydroxyethyl)-D-glucosamine],
poly[N-acetyl-6-O-(ethyl)-D-glucosamine], and
poly(N-acetyl-D-glucosamine) itself
imparts the desired lubricity to rubber and if present in a wound appears to be completely absorbed by living tissue within a surgically acceptable period of time.

Because the biggest use is that of the dusting powder for the surface of the surgeons glove, the present invention will be described in greatest detail in connection with such gloves.

In the glove powder, the lubricity is the key feature and if the rubber glove having the dusting powder on its surface permits ready gloving, that is permits the surgeon to insert his hand into the glove readily, with the glove sliding onto his hand even if somewhat moist, in such fashion as to give the feel to which the surgeon is accustomed, the powder has filled its requirements. It is of course necessary that the glove slide on the surface of the skin of the surgeon sufficiently that the thin rubber membrane does not interfere with the sensitivity of the surgeon's fingers so that the surgeon may readily feel through the glove.

DRAWINGS

In the drawings:

FIG. 1 is a surgical glove having on the surface thereof
a finely divided biodegradable powder consisting essentially of
an enzymatically degradable form of poly(N-acetyl-D-glucosamine) selected from the group consisting of
poly[N-acetyl-6-O-(carboxymethyl)-D-glucosamine],
poly[N-acetyl-6-O-(2'-hydroxyethyl)-D-glucosamine],
poly[N-acetyl-6-O-(ethyl)-D-glucosamine], and
poly(N-acetyl-D-glucosamine) itself
which form of poly(N-acetyl-D-glucosamine) is slowly enzymatically degraded by contact with body tissues.

DESCRIPTION OF THE PREFERRED EMBODIMENTS

Figure 1:
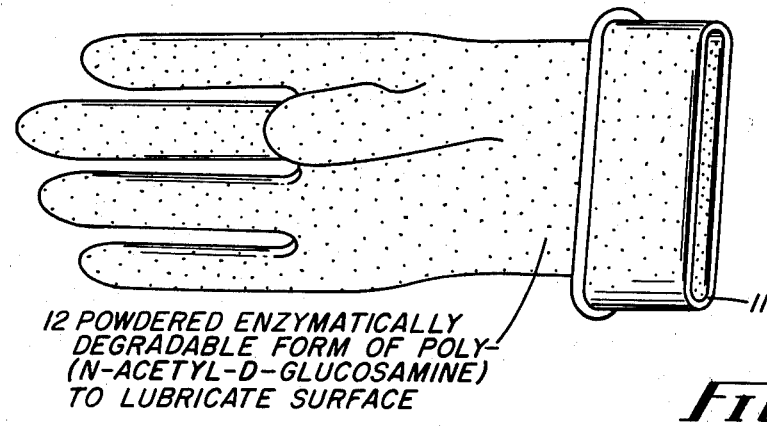

The inventive dusting powder may be prepared by grinding or otherwise pulverizing
a finely divided biodegradable powder consisting essentially of
an enzymatically degradable form of poly(N-acetyl-D-glucosamine) selected from the group consisting of
poly[N-acetyl-6-O-(carboxymethyl)-D-glucosamine], poly[N-acetyl-6-O-(2'-hydroxyethyl)-D-glucosamine],
poly[N-acetyl-6-O-(ethyl)-D-glucosamine], and
poly(N-acetyl-D-glucosamine) itself
to the desired particle size by the use of conventional grinding equipment and techniques known to those skilled in the art.

The polymer may be ground in an ordinary Ball Mill. The grinding equipment is preferably grounded during the grinding operation to prevent undesirable aggregation of the particles caused by the static electrical charges which can accumulate on the particles during grinding. The ground material can then be removed from the mill and vibrated through a series of screens of varying mesh mounted on a Ro-Tap testing sieve shaker as supplied by W. S. Tyler Co.

Particle size of the ground polymer is an important criteria in selecting a powder which is suitable for a glove powder.

It is desirable that all the powder particles be small enough to pass through a 100 mesh screen (149 micron designation in the U.S. Sieve Series). However, small amounts (up to about 1 percent by weight) of somewhat larger sized particles can also be present in the powder without undue adverse effect on the lubricating properties of the polyglycolic acid powder. It is preferred that all of the powder particles pass through a 200 mesh screen (74 micron designation in the U.S. Sieve Series). Passage through such a screen indicates the particles contain not more than one dimension exceeding about 74 microns.

In preparing the glove powder it is equally important that it not be made too fine in order to minimize the escape of escessive powder into the environment in the course of powdering the hands, surgical gloves, or other items. The powder, on the other hand, should not be of an excessively large particle size nor should it contain substantial amounts of exceptionally large particles since this will create an undesirable abrasive effect upon the skin of the hand when the powder is used. A suitable particle size range is from about 0.5 to about 149 microns with a range of from about 10 to 50 microns preferred.

Glove powder is used in a variety of ways by the medical profession. Rubber surgical gloves are typically sold unsterile in pairs with a package of glove powder inserted in the cuff of one of the gloves. When it is desired to use the gloves, the gloves and the package of glove powder are sterilized, usually by autoclaving. The surgeon will then open the package of glove powder (the package usually contains about 1.5 grams of powder) and pour the powder onto his hands. After working the powder over the surface of his hands, the surgeon inserts his powdered hands into the surgical gloves, the glove powder providing the lubricity required to facilitate this insertion. In cases where the gloves are reusable, the gloves, at the end of the operation, will be washed, dried, inspected for holes and then repowdered, usually on both the internal and external surfaces of the glove for subsequent reuse of the glove. This powdering is ordinarily accomplished by placing the gloves and a prescribed amount of glove powder in a tumbler and tumbling for a sufficient period of time to powder the inside and outside surfaces of the glove. The powdered gloves are then repackaged, autoclaved, and presented to the surgeon for use. Since the outside of the glove is often powdered it is readily apparent how some of the powder may spill off the glove and into the exposed surgical cavity of a patient.

Disposable surgical gloves usually made of latex are also available to the medical profession. These gloves can be offered as a unit of one pair of gloves and one package of glove powder contained in a suitable package. However, they are ordinarily offered as a powdered glove, i.e., the inner and outer surfaces of the glove are pre-powdered with a suitable dusting powder. When the contents of the envelope, i.e., the gloves and the powder are sterile, the entire envelope must first be autoclaved or otherwise sterilized. At the end of the operation the gloves are discarded.

Typical glove packages are described in U.S. Pat. Nos. 3,107,786 and 3,181,695.

The gloves of the present invention may be sealed in a strippable enclosure of the type shown in U.S. Pat. No. 2,949,181, there described for sutures, but adaptable to surgical gloves. A larger size strippable laminate enclosure is used for gloves.

From the foregoing it becomes apparent that the glove powder of this invention can be offered either separately in a single package of a suitable material or in combination with a pair of surgical gloves in either a sterile or unsterile condition. The powder itself may be either sterile or non-sterile.

It is desirable when a sterile powdered surgical glove, sterile powder, or a sterile combination of a surgical glove and separately packaged glove powder is to be offered, to package the aforementioned sterile items in a sterile inner enclosure which is then packaged in a sterile outer enclosure. The outer enclosure is provided with a strippable seal, which then allows for convenient serving of said sterile item to the potential user by merely stripping away the outer enclosure to present a totally sterile enclosure, i.e., the outer surface as well as the contents of the inner enclosure are sterile, containing the sterile item to the user. The user can then open the package and remove the sterile item therein without risk of contaminating the contents from contact with the outer surface of the inner enclosure.

Chitin has been estimated to be the second most abundant polysaccharide in nature with a synthesis in the neighborhood of a billion tons a year by marine organisms. See Chitin, N. V. Tracey, Reviews of Pure and Applied Chemistry, Royal Australian Chemical Institute, Vol. 7, No. 1, March 1957, pages 1 to 14.

Carboxymethylchitin is disclosed in Carbohyd, Res. 7, 483–485 (1968), Ralph Trujillo.

This article mentions the hydrolysis of both chitin and carboxymethylchitin by lysozyme.

Poly(N-acetyl-D-glucosamine) differs from cellulose in that instead of a hydroxyl group in the 2 position on cellulose, there is an acetylamino group.

Prudden, Migel, Hanson, Freidrich and Balassa in "The Discovery of a Potent Pure Chemical Wound-Healing Accelerator", The American Journal of Surgery, Vol. 119, May 1970, pages 560 to 564, disclose that chitin containing n-acetyl glucosamine is useful to accelerate wound-healing.

The enzyme lysozyme is particularly effective in the enzymatic degradation of the present forms of poly(N-acetyl-D-glucosamine). Various forms of poly(N-acetyl-D-glucosamine) may have different degradation rates, and the degradation rate may vary with the location, but with minimal tissue reaction. The poly(N-acetyl-D-glucosamine) in its own right has been shown to encourage wound healing.

The lubricant powders of the present forms of poly(N-acetyl-D-glucosamine) are not hydrolyzed by water and, hence, need not be kept bone dry but may be stored under ambient conditions of moisture for prolonged periods of time. The basic poly(N-acetyl-D-glucosamine) may be modified by treatment to introduce carboxymethyl, hydroxyethyl or O-ethyl substituents so that the polymer has linkages from acetyl-6-O-(carboxymethyl)-D-glucosamine units, acetyl-6-O-(2'-hydroxyethyl)-D-glucosamine units, or acetyl-6-O-(ethyl)-D-glucosamine units.

Other side chains may be placed on the glucosamine ring, or its substituents because the side chains may vary from methyl to long chain alkyl, including branched chains, unsaturated chains, aryl or aralkyl, and which may include halogen, alkoxy, aryloxy, aralkoxy, ether, ester and amide groups, as substituents on the side chains, the relative distribution between aqueous and solvent components in a system can be varied as well as water solubility or oil and solvent solubility. Also, because the size and location of the side chains affects the rate of degradation and the acidity of the system, the rate of enzymatic degradation can be varied.

Lubricant powders may be made by precipitating solutions of suitable forms of poly(N-acetyl-D-glucosamine) in polyfluorinated solvents such as hexafluoroisopropyl alcohol and hexafluoroacetone sesquihydrate or mixtures of such solvents.

(N-acetyl-D-glucosamine) has the formula:

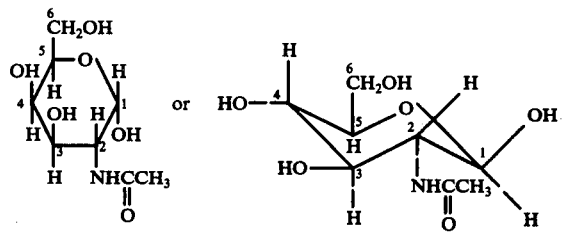

Groups below the plane of the paper are shown by a dotted bond.

Poly(N-acetyl-D-glucosamine) has ascribed to it the formula (ring hydrogens omitted for clarity)

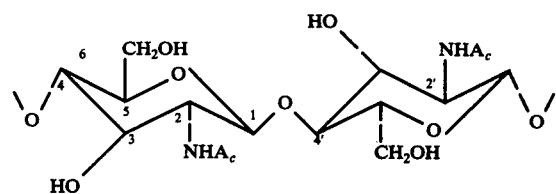

Poly(N-acetyl-D-glucosamine) is a major component of naturally occurring chitin. The naturally occurring material has not only the poly(N-acetyl-D-glucosamine) but also inorganic salts thought to be forms of calcium carbonate and proteinaceous material, the composition of which is not presently known. The term "chitin" is used herein to refer to the various naturally occurring forms of chitin including the protein and inorganic carbonate components. The term "purified chitin" is used to refer to chitin after purification to remove calcium carbonate and other inorganic salts and various proteins which may be present and is essentially poly(N-acetyl-D-glucosamine). Some confusion exists in the literature in that the name chitin is used as a name for poly(N-acetyl-D-glucosamine) without specifying whether it is a naturally occurring material containing inorganic salts and proteins or whether the term is intended to designate purified poly(N-acetyl-D-glucosamine) without specifying the degree of purity or the character of the impurities present.

The term "enzymatically degradable" refers to a form of poly(N-acetyl-D-glucosamine) or its derivatives which is broken down into body fluid soluble components. The problem of retention by the body or disposal is minimal or non-existent.

One convenient method of sterilizing the present lubricant powder is by heat under such conditions that any microorganisms or deleterious materials are rendered inactive. Another common method is to sterilize using a gaseous sterilizing agent such as ethylene oxide. Other methods of sterilizing include radiation by X-rays, gamma rays, neutrons, electrons, etc., or high intensity ultrasonic vibrational energy or combinations of these methods. The present lubricant powders may be sterilized by any of these methods, although there may be an appreciable but acceptable change in physical characteristics.

EXAMPLE 1

Purification of Chitin

A commercial grade of chitin (Cal-Biochemicals) was finely ground in a ball mill overnight to pass a 6 mm screen and be retained by a 1 mm screen. 149 g. of this finely ground material was decalcified by extracting with 825 ml. of 2N HCl at 4° C for 48 hours, in a flask stirred with a magnetic stirrer. The material was collected by centrifugation and washed repeatedly with water until neutral. The ash content was 0.4–0.5%. The decalcified chitin was then stirred at room temperature with 1500 ml. of 90% formic acid overnight. The mixture was centrifuged and the residue repeatedly washed with water. The washed chitin was then suspended in 2 liters of 10% NaOH solution and heated at 90°–100° C. for 2.5 hours. The solution was filtered, the cake washed with water until neutral, washed several times with absolute ethanol and ether, and dried at 40° C. under reduced pressure; yield 66 g. of poly(N-acetyl-D-glucosamine). Infrared spectrum (KBr pellet) shows bands at 3500 cm$^{-1}$ (S), 2900 (W), 1652 (S), 1619 (S), 1550 (S), 1370 (S), 1300 (M), 1070 (Broad). (S is strong, M is medium, W is weak).

EXAMPLE 2

Poly(N-Acetyl-D-Glucosamine) Membranes

Membranes of poly(N-acetyl-D-glucosamine) were prepared by dissolving poly(N-acetyl-D-glucosamine) from Example 1 in each of hexafluoroacetone sesquihydrate (1.4% solution) and hexafluoroisopropanol (2% solution), and casting on a glass plate. The last traces of solvent were evaporated off in a vacuum. The films were tough, transparent, non-tacky, flexible and were quite pliable when hydrated yet retained adequate strength to resist manipulation. The membranes showed no hydrolysis after exposure to water for 5 days.

EXAMPLE 3

Poly[N-acetyl-6-O-(carboxymethyl)-D-glucosamine]

15 g. of the poly(N-acetyl-D-glucosamine) from Example 1 was swollen with 100 ml. of dimethylsulfoxide (DMSO). To this highly swollen suspension was added 400 ml. of 2-propanol and the mixture was stirred vigorously under nitrogen while 40 ml. of 30% aqueous NaOH was added over an interval of 30 minutes at room temperature. After stirring for an additional hour, 18 g. of chloracetic acid dissolved in 40 ml. of water was added dropwise over a 30 minute period. The mixture was then heated at 55° C. for 24 hours. The mixture was decanted and to the residue was added 100 ml. of 70% methanol. The suspension was then neutralized with 5 ml. of 90% acetic acid. The mixture was filtered, washed with 70% methanol, absolute methanol and dried at 40° C. in vacuo. Yield 24 g. of poly[N-acetyl-6-O-(carboxymethyl)-D-glucosamine], I. Infrared (KBr pellet) shows bands at 3500 cm$^{-1}$ (S), 2900 (M), 1600 Broad (S), 1400 (M), 1320 (M), 1100 Broad (S). A sample was titrated and shown to have 4.03 meq acid/g indicating 100% of the repeating mers were carboxylated. Films easily removed from glass were cast from water solution and shown to be transparent, flexible and tough.

EXAMPLE 4

Biodegradability of Poly[N-Acetyl-6-O-(Carboxymethyl)-D-Glucosamine]

After 24 hours incubation at 37° C. in phosphate buffer pH 7.2 containing 1500 units/ml of lysozyme, poly[N-acetyl-6-O-(carboxymethyl)-D-glucosamine] was hydrolyzed to oligomers as determined by Gel Permeation Chromatography. A control containing no enzyme was not hydrolyzed under the same conditions.

EXAMPLE 5

Poly[N-Acetyl-6-O-(2'-Hydroxyethyl)-D-Glucosamine]

Into a screw cap bottle was placed 13.6 g of purified poly(N-acetyl-D-glucosamine) milled so that it passed a 1 mm. sieve. To the bottle was added 200 ml. of cold (0°–5° C.) aqueous 43% NaOH and the contents stirred for 2 hours under nitrogen and then held at 0°–4° C. for 10 hours. The swollen alkali derivative was then squeezed to 3 times its original weight in a sintered glass funnel, disintegrated and frozen at −20° C. under nitrogen for 1 hour and then thawed at room temperature for 1 hour. The freeze-thaw cycle was repeated 3 times. To the alkali derivative was then added 120 ml. of dimethyl sulfoxide (DMSO) and the slurry added immediately to a stirred autoclave. The autoclave was purged several times with nitrogen and 53.2 ml. of ethylene oxide was added (16 equivalents/equivalent of PAG). The mixture was held at 50° C. for 18 hours. The solution was then carefully neutralized with glacial acetic acid, dialyzed and then lyophilized.

The hydroxyethyl derivative can be further purified by precipitating the polymer from aqueous solution with acetone. A freshly precipitated sample of poly[N-acetyl-6-O-(20'-hydroxyethyl)-D-glucosamine] readily dissolved in water, 5% aqueous sodium hydroxide, and 3% acetic acid and is precipitated from these solutions by acetone. Samples analyzed for C, H, and N showed the composition to be one in which 1.5 hydroxyethyl groups had been substituted per glucosamine residue.

EXAMPLE 6

Poly[N-Acetyl-6-O-(Ethyl)-D-Glucosamine]

The procedure of Example 5 was followed except 75 ml. of ethylchloride was added instead of ethylene oxide and the reaction held at 50° C. for 15 hours. A water soluble derivative is obtained.

To obtain an organic soluble derivative, the ethylchloride was mixed with benzene (75% of the amount of ethylchloride). The reaction time was 10 hours and the temperature was controlled as follows: 1 hour heating up to 60° C., 1 hour heating up to 80° C., 1 hour heating up to 130° C. and 7 hours at 130° C. An organic solvent soluble product was obtained. The following solvents are useful for solubilization (5% solution) of this polymer at room temperature: O-xylene, benzene, toluene, methylethyl ketone, 1.4 mixture of alcohol and benzene, chloroform and alcohols.

EXAMPLE 7

The products from each of Examples.

1, 2, 3, 5, and 6 were separately placed in a 1 quart ball mill with about 40 grams of product and five 1¼ inch balls, ten 1 inch balls, nine β inch balls, nine ¾ inch balls and fourteen ⅜ inch balls. The mill was grounded and rotated from a Friday afternoon to a Wednesday morning, about 113 hours; the balls separated and the product screened. About 88 to 90% of the ground product passed a 325 mesh screen with an average particle size of about 25 microns.

A pair of gloves dusted with 1½ grams of each of the product powders were sealed between a polyester, polyethylene laminate as above described using a strippable seal and a group of the gloves were then placed in an ethylene oxide chamber to allow the ethylene oxide to penetrate through the laminate seal as described in more detail in U.S. Pat. No. 2,917,878 Canarius and Kaufman.

The individual gloves before sterilization are indicated in FIG. 1, the surface of the glove 11 has the finely divided biodegradable powder 12 spread thereover.

Figure 2:
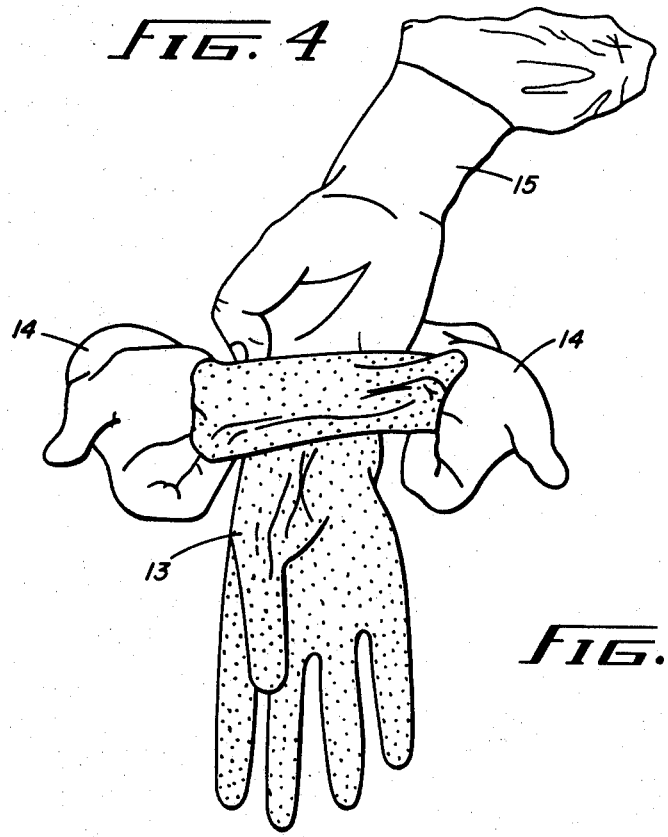
FIG. 2 shows a user donning a surgical glove.

FIG. 2 shows the surgeon donning the glove. The glove 13 is held by a nurse whose hands 14 hold the glove with the cuff slightly stretched while the hand of the surgeon 15 is inserted therein to.

Figure 3:
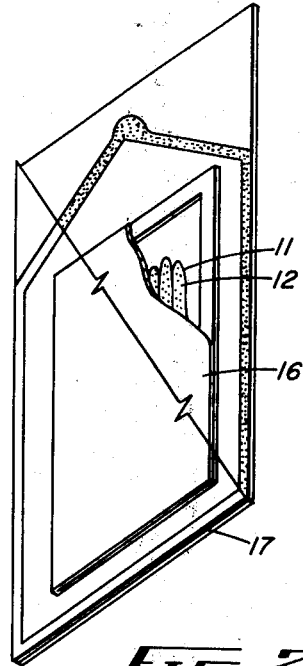
FIG. 3 shows a lubricated surgical glove in a sterile package.

FIG. 3 shows the surgical glove 11, having the powder 12 on its surfaces, folded in a paper wrapper 16, inserted in an outer strippable envelope 17.

It is convenient to powder the glove with the finely divided polymer before the glove is sterilized, and sterilize the powdered glove and keep it in sterile condition until ready for use. It is also convenient to use the powder in sterile form to be applied to the surface of sterile gloves at the time they are being put on. The time of powdering the glove and the time for storing can vary with the technique and schedules of the particular user, such as a hospital or individual surgeon. If sterile gloves are used, a single use disposable glove is convenient. If the gloves are to be reused, the time of applying the powder and the sterilizing can be varied depending upon the number of gloves used in the inventory available or preferences.

When used in patients during surgical procedures, no deleterious effects which could be ascribed to the glove powder were observed.

Figure 4:
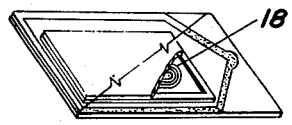
FIG. 4 shows a lubricated catheter in a sterile package.

FIG. 4 shows a catheter 18 similarly packaged in a similar strippable package.

Other sizes and types of ball mills, grinding cycles or systems of attriting may be used with good results. Natural chitin if ball milled to the preferred particle size acts as a satisfactory lubricant — but with various marine and fungal sources, the impurities, particularly the proteins, may vary and have different interactions with tissue. Preferably the chitin is purified and optionally chemically modified and the resultant enzymatically degradable forms of poly(N-acetyl-D-glucosamine) used because of greater freedom from the possibility of tissue reaction.

I claim:

1. A surgical glove of natural or synthetic rubber having on the surface thereof in a small but lubricity imparting quantity
a finely divided biodegradable powder consisting essentially of
an enzymatically degradable form of poly(N-acetyl-D-glucosamine) selected from the group consisting of
poly[N-acetyl-6-O-(carboxymethyl)-D-glucosamine],
poly[N-acetyl-6-O-(2'-hydroxyethyl)-D-glucosamine],
poly[N-acetyl-6-O-(ethyl)-D-glucosamine], and
poly(N-acetyl-D-glucosamine) itself
which form of poly(N-acetyl-D-glucosamine) is slowly enzymatically degraded by contact with body tissues.

2. The glove of claim 1 in which the biodegradable powder has a particle size of 0.5 to 149 microns.

3. The glove of claim 2 in which the glove and powder are sterile, and the powder is poly[N-acetyl-6-O-(carboxymethyl)-D-glucosamine] which will pass through a 200 mesh screen.

4. The glove of claim 2 in which the glove and powder are sterile, and the powder is poly[N-acetyl-6-O-(2'-hydroxyethyl)-D-glucosamine] which will pass through a 200 mesh screen.

5. The glove of claim 2 in which the glove and powder are sterile, and the powder is poly[N-acetyl-6-O-(ethyl)-D-glucosamine] which will pass through a 200 mesh screen.

6. The glove of claim 2 in which the glove and powder are sterile, and the powder is poly(N-acetyl-D-glucosamine) which will pass through a 200 mesh screen.

* * * * *